United States Patent [19]

Welter et al.

[11] Patent Number: 5,147,639
[45] Date of Patent: Sep. 15, 1992

[54] TYPE-C ROTAVIRUS CULTURES AND USES THEREFOR

[75] Inventors: Mark W. Welter, Ubandale; David M. Chambers; C. Joseph Welter, both of Des Moines, all of Iowa

[73] Assignee: Ambico, Inc., Dallas Center, Iowa

[21] Appl. No.: 540,672

[22] Filed: Jun. 19, 1990

[51] Int. Cl.$^5$ .............................................. A61K 39/12
[52] U.S. Cl. ................................ 424/89; 435/237; 435/236; 435/238
[58] Field of Search ................ 435/5, 235.1, 237, 238, 435/236; 424/88, 89, 93

[56] References Cited

U.S. PATENT DOCUMENTS

| | | |
|---|---|---|
| 3,838,004 | 9/1974 | Mebus et al. |
| 3,839,556 | 10/1974 | Mebus et al. |
| 3,869,547 | 3/1975 | Mebus et al. |
| 4,205,131 | 5/1980 | Almeida |
| 4,624,850 | 11/1986 | Albert et al. |
| 4,636,385 | 1/1987 | Plotkin et al. |
| 4,704,275 | 11/1987 | Wyatt et al. |
| 4,751,080 | 6/1988 | Wyatt et al. |
| 4,861,864 | 8/1989 | Atkinson et al. |

OTHER PUBLICATIONS

Bellinzoni, N., Mattion, L., Vallejos, J., LaTorre, E., Scodeller, A. 1987. Atypical Rotavirus in chickens in Argentina. Res. Vet Science, 43: 130–131.

Benfield, D. A., Stotz, Ivan, Moore, R. and McAdaragh, John P. 1982. Shedding of Rotavirus in Feces of Sows Before and After Farrowing. J. Clin. Microbiol., 16: 186–190.

Bohl, E. H., Kohler, E. M., Saif, L. J., Cross, R. F., Agnes, A. G. and Theil, K. W. 1978. Rotavirus as a Cause of Diarrhea in Pigs. J. Am. Vet. Med. Assoc., 172: 458–463.

Bohl, E. H., Saif, L. J., Theil, K. W., Agnes, A. G., and Cross R. F., 1982. Porcine Pararotavirus: Detection, Differentiation from Rotavirus, and Pathogenesis in Gnotobiotic Pigs. J. Clin. Micro., 15: 312–319.

Breer, C., Wunderli, W., Lee, C., Weisser, E., and Schopfer, K., 1985. Rotavirus-und Pararotavirus-Infectionen bei Erwachsenen. Schweiz. med. Wschr. 115: 1530–1535.

Bremont, M., Cohen, J., McCrae, M. A., 1988. Analysis of the Structural Polypeptides of a Porcine Group C Rotavirus. J. Virol., 62: 2183–2185.

Bridger, J. C., Pedley, S., McCrae, M., 1986. Group C Rotaviruses in Humans. J. Clin. Micro. 23: 760–763.

Bridger, J. C. 1988. Porcine Rotaviruses and their Role in Disease. Pig News and Information, 9: 23–26.

Bridger, J. C., 1985. Prevalence of Antibody to Typical and Atypical Rotaviruses in Pigs. Vet. Rec. 116: 50.

Bridger, J. C. 1987. Novel Rotaviruses in Animals and Man. 1987 Novel Diarrhoea Viruses. Wiley, Chichester Ciba Foundation Symposium 128: 5–23.

Brown, D. W., Beards, G. M., Guang-Mu, C., Flewett, T. H., 1987. Prevalence of Antibody to Group B (Atypical) Rotavirus in Humans and Animals; J. Clin. Micro., 25: 316–319.

Brown, D. W. G., Mathan, M. M., Martin, R., Beards, G. M., Mathan, V. I., 1988. Rotavirus epidemiology in Vellore, South India: Group, Subgroup, Serotype, and Electropherotype. J. Clin. Micro. 26: 2410–2414.

Dimitrov, D. H., Estes, M. K., Rangelova, S. M., Shindarov, L. M., Melnick, J. L., and Graham, D. Y. 1983. Detection of Antigenically Distinct Rotavirus from Infants, Infect. and Immun. 44: 2. 523–526.

Espejo, R. T., Puerto, F., Soler, C., and Gonzalez, N., (1984), Characterization of a Human Pararotavirus, Infec. and Immun. 44(1): 112–116.

(List continued on next page.)

Primary Examiner—Christine M. Nucker
Assistant Examiner—Jeffrey Stucker
Attorney, Agent, or Firm—Iver P. Cooper

[57] ABSTRACT

Type-C rotavirus are propagated in swine testicular cells with reduced concentrations of proteolytic enzyme for subsequent production of antigen and antiserum for use in diagnostic kits and for killed vaccines to prevent Type C rotavirus infections. Propagation of Type C rotavirus in the ST cells can also lead to virus modification for subsequent use as a modified live virus vaccine to prevent Type C rotavirus infections.

19 Claims, 2 Drawing Sheets

OTHER PUBLICATIONS

Fitzgerald, G. R., Welter, M. W. and Welter, C. J. 1986. Evaluating the Performance of a Porcine Rotavirus Vaccine. Vet. Med., 81: 188–192.

Fitzgerald, G. R., Welter, M. W. and Welter, C. J. 1986. Effect of Porcine Rotavirus Vaccination on Postweaning Weight Gains in Baby Pigs. Modern Vet. Pract., 67: 609–610.

Fitzgerald, G. R., Barker, T., Welter, M. W. and Welter, C. J. 1988. Diarrhea in Young Pigs: Comparing the Incidence of the Five Most Common Infectious Agents. Vet. Med., 83: 80–86.

Jashes, M. Sandino, A. M., Faundez, G., Avendano, L. F., Spencer, E., 1986. In Vitro Transcription of Human Pararotavirus. J. Virol. 57: 183–190.

Kapikian, A. Z., Fores, J., Hoshino, Y., Midthun, K., Gorziglia, M., Green, K. Y., Chanock, R. M., Potash, L., Sears, S. D., Clements, M. L., Halsey, N. A.., Black, R. E., Perez-Schael, I., 1989. Prospects for Development of a Rotavirus Vaccine Against Rotavirus Diarrhea in Infants and Young Children. Rev. of Infect. Dis. vol. II, Supplement 3:s539–546.

Matsumoto, K., Motoichi, H., Shudo, Y., Shuji, N., Shunzo, C., and Yoshinobu, K. 1989. An Outbreak of Gastroenteritis Associated with Acute Rotaviral Infection in School children. J. of Infect. Dis. 160(4): 611–615.

Nagesha, H. S., Hum, C. P., Bridger, J. C., Holmes, I. H., 1988. Atypical Rotaviruses in Australian Pigs. Arch. Virol. 102: 91–98.

Nicolas, J. C., Cohen, J., Fortier, B., Lourenco, M. H., and Bricout, F. 1982. Isolation of a Human Pararotavirus. Virology 124: 181–184.

Ojeh, C. K., Saif, L. J., Kang, S. Y., 1988. Production and Characterization of Monoclonal Antibodies to Procine Group C Rotavirus. Conference of Research Workers in Animal Disease, Nov. 14–15, Abstract #328.

Pedley, S., Bridger, J. C., Brown, J. F., McCrae, M. A., 1983. Molecular Characterization of Rotaviruses with Distinct Group Antigens. J. Gen. Virol., 64: 2093–2101.

Penaranda, M. E., Cubitt, W. D., Sinarachatanant, P., Taylor, D. N., Likanonsakul, S., Saif, L., Glass, R. I., 1989. Group C Rotavirus Infections in Patients with Diarrhea in Thailand, Nepal and England. J. Infect. Dis. 160: 392–397.

Rodger, S. M., Bishop, R. F., Holmes, I. H., 1982. Detection of a Rotavirus-Like Agent Associated with Diarrhea in an Infant. J. Clin. Micro. 16: 724–726.

Saif, L. J., and Theil, K. W., 1985. Antigenically Distinct Rotaviruses of Human and Animal Origin. Elsevier Science Publishers B.V. Infectious Diarrhea in the Young. 208–214.

Saif, L. J., Terret, L. A., Miller, K. L., and Cross, R. F. 1988. Serial Propagation of Porcine Group C Rotavirus (Pararotavirus) in a Continuous Cell Line and Characterization of the Passaged Virus. J. of Clin. Micro. 26(7): 1277–1282.

Snodgrass, D. R., Herring, A. J., Campbell, I., Inglis, J. M., Hargreares, F. D. 1984. Atypical Rotaviruses from Calves, Piglets, Lambs and Man. J. Gen. Vir., 65: 909–914.

Terret, L. A., and Saif, L. J., (1987), Serial Propagation of Porcine Group C Rotavirus (Pararotavirus) in Primary Porcine Kidney Cell Culture, J. Clin. Micro., 25: 1316–1319.

Terret, L. A., Saif, L. J., Theil, K. W., and Kohler, E. M. 1987. Physicochemical Characterization of Porcine Pararotavirus and Detection of Virus and Viral Antibodies Using Cell Culture Immunofluorescence, J. Clin. Micro. 25(2): 268–272.

Theil, K. W., McCloskey, C. M., Saif, L. J., Redman, D. R., Bohl, E. H., Hancock, D. D., Kohler, E. M., Moorhead, P. D. 1981. Rapid, Simple Method of Preparing Rotaviral Double-Stranded Ribonucleic Acid for Analysis by Polyacrylamide Gel Electrophoresis. J. Clin. Micro. 14: 273–280.

Ushijima, H., Honma, H., Mukoyama, A., Shinozaki, T., Fujita, Y., Kobayashi, M., Ohseto, M., Morikawa, S., and Kitamura, T., (1989), Detection of Group C Rotaviruses in Tokyo, J. of Med. Vir. 27: 299–303.

Von Bonsdorff, C., Svensson, L., Human Serogroup C Rotavirus in Finland, (1988), Scand. J. of Infect. Dis. 20: 475–478.

Welter, M. W., Welter, C. J., Evaluation of Killed and Modified Live Porcine Rotavirus Vaccines in Cesarean Derived Colostrum Deprived Pigs. Vet Micro. "In Press".

Woode, G. N., Bridger, J. C., Hall, G. A., Jones J. M. and Jackson, G. 1976. The Isolation of Reovirus-Like Agents (Rotaviruses) from Acute Gastroenteritis of Piglets. J. Med. Microbiol., 9: 203–209.

Welter, M. W., Fitzgerald, G. R., and Welter, C. J. 1986. A Combination Porcine Rotavirus Vaccine Against Two Major Type-A Serotypes. Agri. Practice Swine Immunology. 7: 59–62.

ELECTRONMICROGRAPH OF CELL CULTURE PASSAGE TYPE C ROTAVIRUS REACTED WITH ANTIBODY

FIG. 2.

TYPE-C ROTAVIRUS CULTURES AND USES THEREFOR

CROSS-REFERENCE TO RELATED APPLICATION

Mark W. Welter, David M. Chambers and C. Joseph Welter filed an application entitled TYPE-B ROTAVIRUS CULTURES AND USES THEREFOR on Nov. 13, 1989, Ser. No. 07/434,209. This application is commonly owned.

FIELD OF THE INVENTION

The present invention relates to propagation of Type-C rotaviruses in a diploid cell culture with reduced concentrations of proteolytic enzyme and subsequent production of antigen and antiserum for use in diagnostic kits and production of vaccines, both modified live and formalin killed, to prevent Type-C rotavirus infections.

BACKGROUND OF THE INVENTION

Rotavirus is the leading cause of viral gastroenteritis in infants and piglets (2, 3, 4, 7, 8, 9, 17, 20, 27, 37). Rotaviruses, which are found in a great variety of animal species, are named for their characteristic wheel-like appearance under the electron microscope. Like other Reoviridae, their genome is in the form of double-stranded (ds) RNA, although they may be distinguished from reoviruses and orbiviruses by the division of their genome into 11 ds RNA segments.

In 1983, Pedley (24) classified the rotaviruses into several types of groups on the basis of serological differences, immunofluorescence, and nucleic acid differences characterized by one dimensional terminal fingerprint analysis. RNA electropherotype has also been used as a basis for classification (29). Group A rotaviruses are considered "typical"; all others (B, C, D, E) are referred to as "atypical." Type-C (Group-C) rotaviruses, sometimes referred to as pararotavirus, have been found to produce gastroenteritis in chickens, pigs, and also in humans (1, 4, 5, 7, 10, 11, 12, 13, 14, 20, 21, 22, 25, 26, 33, 34). A panel of sixteen monoclonal antibodies have been made to the porcine Type-C rotavirus (Cowden strain), with four of these having neutralizing capabilities. Only Type-C antigens were detected by the monoclonal antibodies tested, and no reactions were seen with Type-A or Type-B rotaviruses (23).

Analysis of the structural polypeptides of porcine Type-C rotavirus by Western blot analysis has revealed that there is a lack of cross-reaction between the structural polypeptides of porcine rotaviruses Types A, supporting the fact that both are distinctly different from each other, and thus the different serogroup classification (6, 18, 23).

Type-C rotavirus has been implicated as a cause of diarrhea in nursing and weakling pigs (4, 8, 15, 17, 21). Diagnostic surveys, conducted over several years, have revealed that Type-C rotavirus infections are responsible for 25% of preweaning scours cases and 40% of postweaning scours cases where rotavirus was deemed to be the causative agent (17). In Australia, 7 out of 235 cases of rotavirus diarrhea were linked to Type-C rotavirus by gel electrophoresis (21).

There is additional evidence of Type-C rotavirus prevalence as measured by Type-C, specific serum antibody. In Ohio, 100% of adult pigs, 59% of weaning pigs, and 86% of nursing pigs showed exposure to Type-C rotavirus, as measured by serum antibody levels (Specified Indirect Immunofluorescence; IFA, 31). In the United Kingdom, 58–90% of piglets from three to twenty-six weeks old had positive Type-C antibody titers as measured by IFA, whereas 77% of adult swine showed previous exposure to Type-C by IFA (9, 11).

Porcine Type-C rotavirus has been found to cross-react with at least eight different isolates of Human Type-C rotavirus by Immune Electron Microscopy (IEM) and IFA serological assay, suggesting that one common group antigen exists between porcine and human Type-C rotavirus strains (7, 10, 12, 20, 25, 26, 27, 33, 34).

Type-A rotaviruses have been successfully propagated in several different cell lines, but they require incorporation of either proteolytic enzymes, DEAE dextran, or a combination of both. Use of increased virus inoculum volumes has also contributed to the success in growing some of the type-A human rotavirus strains (42). Type-A-Rotavirus diagnostic kits, and bovine and porcine Type-A Rotavirus modified live virus vaccines are commercially available (38, 39, 40, 15 16, 35, 36). Human vaccines have been developed but not commercialized.

Limited replication of porcine Type-C rotavirus (Cowden strain) has been demonstrated in two types of cell cultures: Primary Pig Kidney (PK) and embryonic Rhesus Monkey Kidney (Ma-104) (28, 30). The intestinal origin Type-C rotavirus was maintained in PK cells for 17 passages by incorporating high (cytotoxic) levels of proteolytic enzyme (pancreatin, 30) e.g., 80–120 µg/ml. Pancreatin is a mixture of several enzymes consisting of proteases (e.g., trypsin, chymotrypsin, alpha trypsin, etc), lipases, and amylases. Type-C rotavirus PK pass-9 was used as the inoculum for subpassage in Ma-104's. Again, high levels of pancreatin were required for maintenance of the virus. At these high levels of pancreatin, viral cytopathic effect (CPE) was not readily observed, due to the cellular toxic effect (e.g., detachment of the cells) of the proteolytic enzymes on the cell cultures. (When only 40 µg/ml pancreatin was used, virus growth ceased after 3 passages.) The PK-passaged Type-C rotavirus was then passaged in the Ma-104's eighteen times, resulting in a peak titer of $5 \times 10^6$ fluorescent focus units/ml at the sixteenth passage.

However, none of the cell culture passes have been reported to contain virus titers higher than $5 \times 10^6$ FFU/ml (Fluorescent Foci Units). In addition, the 22nd and 26th cell culture passages were fed to gnotobiotic pigs by these workers and were still found to be pathogenic. Animals developed diarrhea and demonstrated villious atrophy. Propagation of porcine Type-C rotavirus in Ma-104 cell cultures directly from intestinal contents of infected pigs was unsuccessful (28). Attempts by other laboratories to propagate Type-C rotaviruses in cell culture, using either the reported Type-C techniques or the previously reported techniques used in growth of Type-A's have been unsuccessful (28, 30, 31, 33). The use of primary tissue culture (PK) for growing viruses suffers from the disadvantage that the primary tissue cultures are prone to contamination with not easily detected viruses, and the probability of which cannot be thoroughly established prior to actual use of the primary tissue. Thus, vaccine production in primary tissues are susceptible to extraneous virus contaminations which may not be detected until well after the preparation of the vaccine component.

It is obvious from epidemiological studies in swine (8, 9, 17, 31) that there is a need for an effective vaccine be it either inactivated or attenuated. There is also a need for development of diagnostic aids for detecting Type-C rotavirus infections. A process of cultivating Type C rotavirus for numerous passages at high viral titer, preferably attenuating the virulence of the virus without substantial loss of immunogenicity, is therefore sought.

All references are incorporated by reference to the extent pertinent. No admission is made that any reference constitutes prior art.

SUMMARY OF THE INVENTION

It is an object of the present invention to overcome the aforementioned deficiencies in the prior art.

It is another object of the present invention to adapt virulent Type-C rotavirus for growth in culture.

It is yet another object of the present invention to produce antigen for use in diagnostic kits for Type-C rotavirus.

It is still a further object of the present invention to produce antiserum for use in diagnostic kits for Type-C rotavirus.

It is a further object of the present invention to produce modified live vaccines to prevent Type-C rotavirus infections.

It is another object of the present invention to produce formalin killed vaccines to prevent Type-C rotavirus infections.

It is still a further object of the present invention to serially propagate Type-C rotavirus in swine testicular cells in the presence of reduced (non-cytopathic) amounts of proteolytic enzymes in order to produce large quantities of viral antigen for use in diagnostic tests or as vaccines. The resulting modified live virus is non-pathogenic, even when backpassaged in the original host species, but is nonetheless immunogenic for at least 55 additional passages in ST cells.

According to the present invention, virulent Porcine Type-C rotavirus, derived from the intestinal contents of infected pigs, is adapted to grow in an established swine diploid cell line, Swine Testicular (ST) cells. This method allows for growth of the Type-C rotavirus at high titers and maintenance in cell culture.

Type-C rotavirus growth produces a cytopathic effect in swine testicular cells similar to that seen when swine testicular cells are infected with Type-A rotaviruses. This cytopathic effect is characterized by cellular stranding and subsequent cell lysis with some of the infected cells occasionally clinging to the monolayer by a thin thread of cellular debris. This phenomenon has been referred to as cellular flagging.

Type-C rotavirus infection in swine testicular cells was confirmed by specific indirect immunofluorescent (IFA) staining of infected cultures or by RNA extraction and polyacrylamide gel electrophoresis (PAGE) evaluations of the harvested fluids.

Although Type-C rotavirus growth in primary pig kidney and in Ma-104 cells (Fetal Rhesus monkey kidney) has been reported previously (28,30), the growth as disclosed in these references requires high levels of proteolytic enzymes and virus yields are relatively low, and the viral cytopathic effect is obscured by the CPE of pancreatin itself.

The present invention, in which Type-C rotavirus is adapted to swine testicular cells, in the presence of trypsin alone, and in nontoxic amounts (10–20 $\mu$g/ml), has significantly increased viral yields which can be conveniently quantified by the cytopathic effect upon the swine testicular cells. The present invention is directed to a method for serially propagating Type-C rotavirus in swine testicular cells in the presence of reduced amounts of proteolytic enzyme (preferably less than 80 $\mu$g/ml and more preferably about 20 $\mu$g/ml) so as to produce large quantities of viral antigen for use in diagnostic tests or as vaccines.

Convalescent serum to Human Type-C rotavirus and to porcine Type-C rotavirus have been found to cross react with each other, suggesting a relationship between the two strains of Type-C rotavirus. In addition, hyperimmune serum to porcine Type-C rotavirus has been reported to cross react with several strains of human Type-C rotavirus (7, 10, 12, 20, 25, 26, 27, 33, 34). Because of this phenomenon, the cell culture adapted porcine Type-C rotavirus of the present invention can serve as an indicator virus for production of antiserum and as an antigen source for use in diagnostic kits. In addition, the cell culture adapted porcine Type-C rotavirus described herein is also useful as a vaccine for Type-C rotavirus infections in other nonporcine species.

By manipulation through serial passage in swine testicular cells, Type-C rotavirus loses its virulence, but maintains antigenicity (modified live virus) as tested in the host animal. The examples given below clearly demonstrate that Type-C modified live rotavirus (MLV) replicates in inoculated animals without associated virulence, resulting in subsequent protection from challenge with virulent porcine Type-C rotavirus (active immunization).

In addition, MLV Type-C rotavirus and formalin killed Type-C rotavirus, both generated by passage in swine testicular cells, have been used to effectively immunize pregnant swine to Type-C rotavirus, thus allowing for increased colostral and milk antibodies provided to nursing baby pigs, the primary animal susceptible to Type-C rotavirus infections. This acquired immunity is referred to as passive immunity, and will only protect nursing animals from infection as long as milk antibody titers are high enough and the animals continue to nurse.

While the propagation of a porcine Type-C rotavirus in cell culture is specifically exemplified, it will be understood that the method can be adapted to the Type-C rotavirus of other species, including humans, bovines and other species.

Thus, the present invention provides a method for serially propagating Type-C rotavirus to produce either a modified live or a killed vaccine that can be used in the prevention of Type-C rotavirus disease in humans or animals.

BRIEF DESCRIPTION OF THE DRAWINGS

These and other objects, features, and many of the attendant advantages of the invention will be better understood upon a reading of the following detailed description of the invention when considered with the accompanying drawings herein.

DETAILED DESCRIPTION OF THE INVENTION

The above objects and advantages of the present invention are achieved as illustrated by the nonlimiting examples set forth herein.

Continuous cell lines (Ma-104) are usually aneuploid with a subtetraploid karyotype, and contain chromosomes displaying structural anomalies. A continuous cell line, while theoretically having an infinite life, is undesirable for virus propagation, since it has become "transformed", i.e., the chromosome composition has become deviant and carries within it the potential of tumorigenic or oncogenic properties.

ST cells are a swine diploid cell line whose purity from contaminants (bacterial, mycoplasma, and extraneous viruses) and chromosomal stability (no chromosomal anomalies) has been determined according to government guidelines. The cells have been registered for vaccine production by the U.S.D.A. In addition, these cells have been found to be nontumorigenic.

The ST diploid cell line has been found to be highly susceptible for a wide range of porcine viruses including: Parvovirus, Transmissible Gastroenteritis, Adenovirus, and Rotaviruses, Type-A, Type-B, and Type-C. In addition to all of the above listed advantages for use of ST cells over PK's or MA-104's, the most outstanding advantage is the fact that after as little as 25 passages in ST's with procedures described herein, the Type-C rotavirus lost its pathogenicity for pigs but remained antigenic, a finding which has not previously been reported.

Heretofore, a Type-C rotavirus has not been successfully grown and passaged in diploid cells or in swine testicular cells. The cell culture adapted Type-C rotavirus provides a distinct advantage over human strains because of its lack of pathogenicity. Results of indirect immunofluorescent staining of infected cell cultures clearly establish the antigenic relationship between the two strains.

It is believed that at least some of the advantages of the swine testicular diploid cell line extend to other diploid cell lines, and the use of other diploid cell lines is contemplated to the extent that they are capable of supporting the growth of Type C rotavirus. If a continuous (stable) cell line can support such growth, it, too, may be used, though with the caveats previously stated.

In practicing the present invention, any materials and methods equivalent to those described herein can be used, although the preferred choices are presented hereunder.

The isolate herein designated Ambico Type-C, strain-1 (AmC-1) is available from the American Type Culture Collection as ATCC UR-958. It was provided to ATCC by Dr. E. H. Bohl as a 20% suspension of intestinal contents ("bulk intestinal fluids") from gnotobiotic pigs inoculated with a viral isolate. Any animal with a Type C rotavirus infection may be used as an alternative source of a Type C rotavirus isolate.

Figure 1:
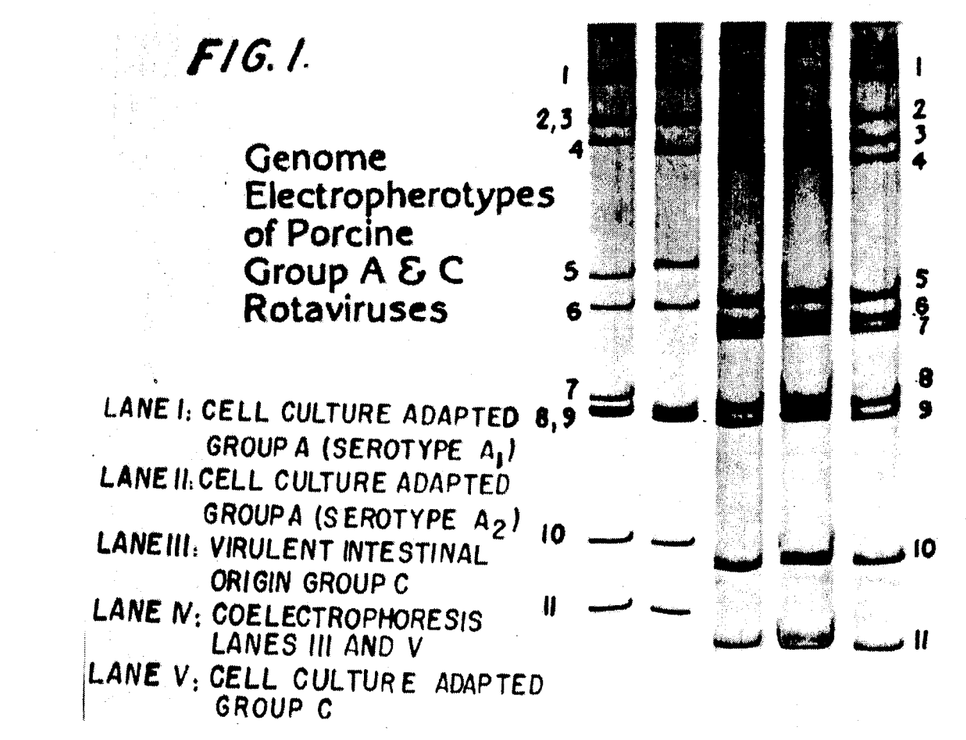
FIG. 1 shows the virus genomes ("fingerprint") of a porcine Type-C rotavirus isolate by means of the RNA extraction and PAGE analysis technique (32). Both the virulent (intestinal origin parent) and cell culture adapted (passage 50) isolates show the same fingerprint. The cell culture passages used swine testicular cells.
Figure 2:
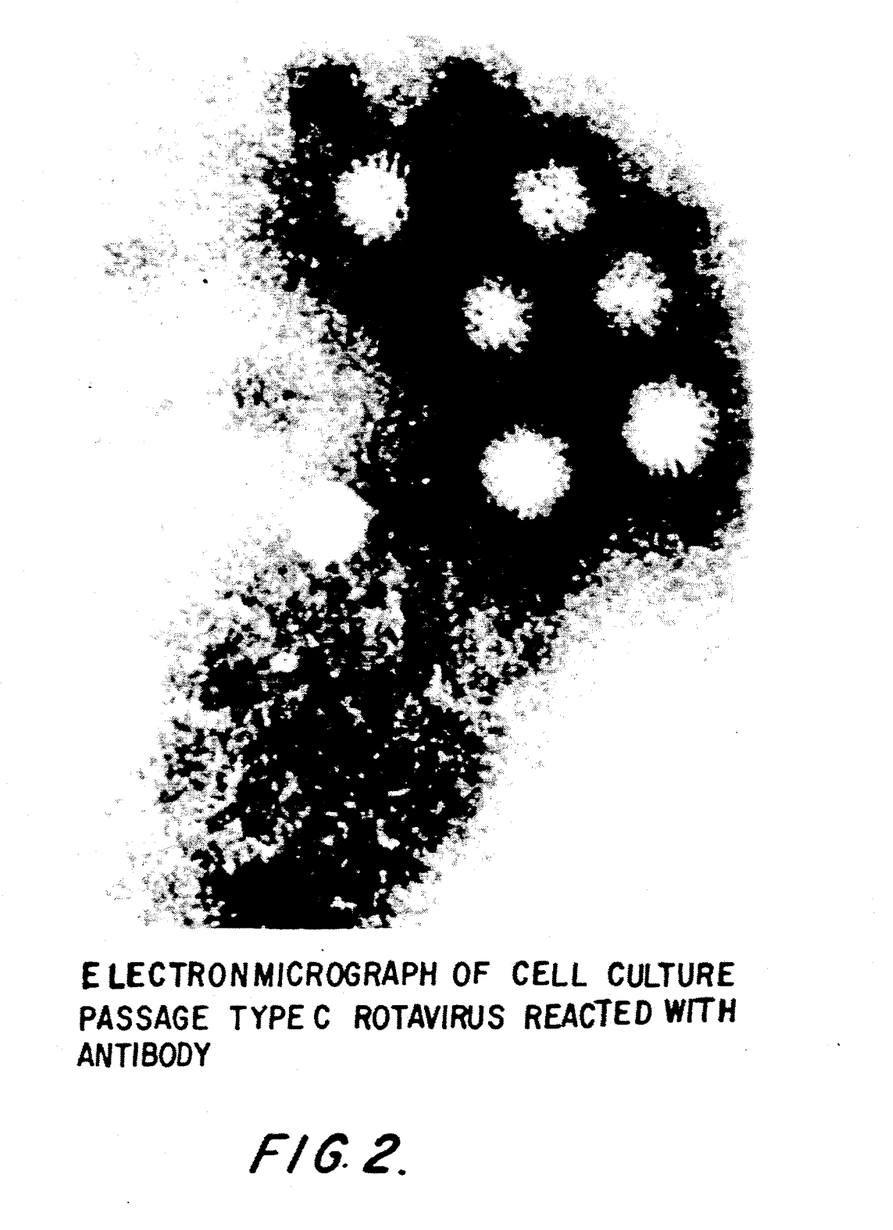
FIG. 2 is an immune electron micrograph of the 50th pass of the porcine Type-C rotavirus in swine testicular cells, demonstrating the virus to have maintained its antigenicity through cell culture passage.

This isolate was passed three times in gnotobiotic pigs at which time a large bulk pool of fluids was generated from infected intestinal contents. This isolate was purified by centrifugation and filter sterilization. Only Type-C rotavirus was identified by the third passage in pigs. Its purity and identity was demonstrated by (a) specific indirect IFA staining of small intestinal sections of challenged sacrificed animals (16 hours post-challenge); (b) viral genome profile by RNA extraction PAGE evaluation of intestinal contents, as shown in FIG. 1; and (c) immunoelectron microscopy of intestinal contents. Purity was further demonstrated as the intestinal contents were used to produce hyperimmune serum in colostrum deprived Cesarean derived (CDCD) pigs, and only activity to Type-C rotavirus was detected in the serums post-hyperimmunization.

While this example describes propagation in ST cells of a viral isolate previously passaged in gnotobiotic pigs, we have found in further experiments that field strains of Type C may be passaged directly in ST cells. Preliminary passages in live animals may be desirable to amplify viral titers or to eliminate adventitious infections.

Virulence of the Type-C bulk virus was demonstrated in CDCD pigs. Challenged pigs developed watery diarrhea within 24 hours post-inoculation, and it persisted for 5 to 7 days post-challenge. Small intestinal segments taken from pigs sacrificed at 16 to 18 hours post-challenge revealed a stunted appearance of the small intestinal villi (villous atrophy). Frozen sections stained by IFA revealed diffuse areas of infection on the distal tips of the villi with predominate infection occurring in the duodenum and jejunum of the intestine. The lumen of the small intestine was full of water contents, and challenged animals demonstrated a decreased average daily weight gain compared to nonchallenged controls. The pig infectious dose (PID) was determined to be $10^3$ $PID_{50}$/ml with a duration of 5 to 7 days.

The bulk intestinal fluids described earlier were used as starting material for growth in cell culture. The swine testicular cells (54th passage level) were obtained from Dr. Arlin McClurkin, National Animal Disease Laboratory. Swine testicular cells at passage level 114 are available from the American Type Culture Collection as ATCC CRL 1746. These ST cells were supplied by McClurkin to ATCC.

Procedures for adapting Type-C rotavirus to primary pig kidneys and Ma-104 cells have been reported previously (28, 30). In these studies, toxic or just subtoxic amounts of proteolytic enzyme (pancreatin) were required to facilitate growth. For adaptation to swine testicular cells, only trypsin was incorporated into the virus maintenance medium at a concentration of about 5–80 μg/ml, and preferably about 10–20 μg/ml. This is a distinct advantage over previous reports where Type-C rotavirus cytopathic effect in Ma-104 cells was obscured by the cytotoxic effect of the amounts of pancreatin used. By incorporating trypsin at only the 10–20 μg/ml level, viral cytopathic effect could be readily observed. For the first five serial passages in swine testicular cells it was desirable to concentrate the virus between passages. Briefly, the virulent virus bulk described above was inoculated into a roller bottle of swine testicular cells with the methods described in Example 1. After 48 hours post-inoculation, no cytopathic effect was evident. The cells and virus propagation medium were frozen and thawed three times, and then the entire contents of the bottle were centrifuged at 100,000 × g. The pellet was resuspended in fresh virus propagation medium and reinoculated into another swine testicular roller bottle. This procedure was repeated for five serial passages in swine testicular cells. By the fifth passage, the cytopathic effect was evident, 
and Type-C rotavirus was identified in the virus propagation medium by RNA extraction PAGE analysis. At this point, no further concentration of the virus bulk was necessary to continue passage in swine testicular cells.

Example 1

Virus propagation and serial passage in an established diploid swine testicular cell line The medium used for virus propagation consisted of Eagle's minimal essential medium with nonessential amino acids and L-glutamine in Earles BSS, 0.1M sodium pyruvate, pH adjusted to 7.2 with sodium bicarbonate. Just prior to use, the basal medium was further supplemented with 0.2M HEPES buffer, 50 μg/ml of gentamicin, 10–20 μg/ml trypsin, and the pH was adjusted to 7.4 with 10N sodium hydroxide. It is permissible to incorporate other proteolytic enzymes instead of or in addition to trypsin, provided that they are restricted to a level such that their cytotoxic effect does not obscure viral cytopathology. For example, pancreatin at a level of 1–20 μg/ml, preferably 10 μg/ml. The use of DEAE-dextran during viral adsorption and incorporated into the virus propagation medium was found to increase the rate of cytopathic effect but was not found to increase virus titers significantly. The level of DEAE-dextran used was 0.05 to 0.1 μg/ml. The cell cultures were rinsed with virus propagation medium three times and incubated at 37@C. for 30 to 60 minutes prior to inoculation. The cell culture vessels that were used for virus propagation include microtiter plates, tissue culture tubes, Leighton tubes, 32 ounce bottles, and 640 $cm^2$ roller bottles. Rolling was found to be the most effective method for generating virus. Stationary cultures usually did not exhibit cytoplasmic effect, but upon evaluation by IFA were found to be infected, demonstrating typical cytoplasmic fluorescence.

Virus fluids for inoculation can be pretreated with as much as 500 mg of trypsin, or with 0.1% sodium dodecyl sulfate (SDS), prior to inoculation. Pretreatment was not found to hinder virus replication, and has not been found to increase or decrease significantly virus titer or viral adaptation to cell culture.

After the rinse medium was removed, the cultures were inoculated with Type-C rotavirus and incubated at 37°–39° C. for one to two hours. The inoculum was either rinsed off or simply diluted with fresh virus propagation medium. The cultures, either rolled or stationary, were incubated at 37–39@C. for from one to ten days. Infected cultures exhibit cytopathic effect as early as 14 hour post-infection, with focal areas of infection increasing in size with time.

Cytopathic effect was characterized by cellular stranding and subsequent cell lysis, with some of the infected cells occasionally clinging to the monolayer by a thin thread of cellular debris. The cytopathic effect progresses to the point where all cells are involved and cell lysis is seen throughout the entire monolayer. Multiple virus harvests can be made during the cytopathic effect cycle, thus allowing for large quantities of virus. At this point the virus may be stored in liquid, frozen, or lyophilized form. The usual virus titer achieved by this method is about $10^{7.5}$ to about $10^{9.5}$ Tissue Culture Infectious $Dose_{50}$ ($TCID_{50}$) per ml. Preferably, the virus is passaged at least 30 times. Pathogenicity is usually lost by the 22nd passage. This inoculation, incubation, and harvest of cell cultures has been continued for fifty times without effect upon the virus genome or its antigenicity, as shown in FIGS. 1 and 2.

| Type-C rotavirus Passage level in ST's | Amount of Virus Present ($TCID_{50}$/ml) | Type-C Identification IFA[1] | GE[2] |
|---|---|---|---|
| AmC-a/ST-1 | No CPE | + | + |
| AmC-1/ST-10 | $10^5$–$10^6$ | + | + |
| AmC-1/ST-25 | $10^8$–$10^9$ | + | + |
| AmC-1/ST-50 | $10^8$–$10^9$ | + | + |

[1]IFA: Indirect Immunofluorescent Staining
[2]GE: RNA extraction PAGE evaluation: Rotavirus Fingerprint analysis Example 2

Diagnostic Use

Antiserum to the human Type-C rotavirus will cross-react with the porcine Type-C rotavirus and porcine Type-C antiserum will cross-react with human Type-C rotavirus as evaluated by specific IFA and immune electron microscopy (IEM) assays. In addition, published results indicate that at least eight isolates of human Type-C rotavirus from different countries will cross-react with the porcine Type-C rotavirus (7, 10, 12, 20, 25, 26, 27, 33, 34).

Two sources of human Type-C rotavirus antiserum were evaluated. The convalescent serum was provided by Dr. Lennart Svensson, Veterans Medical Hospital, Standford University. Swine testicular cells growing on microtiter plates were inoculated with AmC-1 pass 52 as described in Example 1. The infected cells were fixed in acetone and stained by indirect immunofluorescence using different dilutions of the human Type-C antisera. It should be understood that since Type C rotavirus is cytopathic the fixed material included cell-free viral particles which could be bound by an antibody. Potential alternative fixatives include methanol, ethanol, propanol, Bouin's, Zenker's, glutaraldehyde, and formalin. The fixative must not substantially reduce antigenicity. Anti-human IgG-fluorescent isothiocyanate (FITC) was used as conjugate. Other fluorescent labels, such as rhodamine, may be substituted for the FITC.

Specific cytoplasmic fluorescence was seen at a 1/10 and 1/100 dilutions, but not at 1/1000. Thus, it was possible to detect the presence of human antibodies responsive to a human Type C rotavirus infection using a antigenic reagent prepared from ST cells infected with a porcine Type C rotavirus.

An antigen capture ELISA was evaluated using antiserum to Type-C rotavirus prepared in goats and guinea pigs. Type-C rotavirus bulk fluids propagated in swine testicular cells as described in Example 1 were used as the immunizing agent for production of antiserum. The virus fluids were frozen and thawed three times and the cell debris removed by centrifugation at 10,000×g for 30 min. The virus was further purified by ultracentrifugation (100,000×g for 2 hours) through a sucrose gradient. Virus was collected and resuspended in sterile water. To remove any excess sucrose the virus was ultracentrifuged again as above and this time virus pellet was resuspended in sterile water.

Animals were hyperimmunized with virus adjuvanted in Freund's complete adjuvant, over a period of six weeks, with injections at one, three and five weeks.

Antiserum titers to the Type-C rotavirus were determined by ELISA block titrations against the purified Type-C rotavirus antigen described above using either anti-guinea pig or anti-goat IgG peroxidase conjugate and ABTS substrate.

The assay used for Type-C rotavirus detection was a sandwich ELISA where the microtiter plate was coated with a desired dilution of goat anti-Type-C rotavirus and incubate at 4° C. overnight. The plates were washed with physiological saline and nonbound sites were blocked using 2% fetal bovine serum. The plates were washed with physiological saline and then inoculated with four fold dilutions (in physiological saline) of Type-C rotavirus bulk fluids generated as described in Example 1. As a control the last row of each plate was inoculated with four fold dilutions of Type-A rotavirus. After incubation for 1-hour at room temperature the plates were washed with physiological saline and Type-C guinea pig antiserum was added. After incubation for 1-hour at room temperature the plates were washed with physiological saline and rabbit anti-guinea pig horse radish peroxidase was added to all the wells. After a 1-hour incubation at room temperature, the plates were washed with physiological saline and ABTS substrate was added to each well. After incubation at room temperature in the dark for 1-hour the plates were read on an ELISA reader with a 410 nm filter. A positive reading was determined by samples giving a specific color reaction≧0.1 optical density unit.

Example 3

Vaccine Evaluation of Tissue Culture Adapted Type-C Rotavirus: Active Immunity

Experiments were conducted to determine if the Type-C cell culture adapted rotavirus was still virulent for pigs. Studies in which the virus was backpassaged in CDCD pigs for a total of five times demonstrated no reversion to virulence. The safety of the vaccine has also been demonstrated by inoculation of guinea pigs, mice, rabbits, baby pigs, and pregnant swine. No adverse reactions due to vaccination were demonstrated in any of the animals.

An animal vaccine study was conducted in order to determine if the cell culture adapted porcine Type-C rotavirus maintained its immunogenicity after 50 passages in swine testicular cells with this technology. Ten CDCD pigs were used to evaluate different cell culture passage levels of adapted Type-C porcine rotavirus. Two animals were nonvaccinated controls, four animals were vaccinated with Type-C rotavirus ST passage 25, and four were vaccinated with Type-C rotavirus ST passage 50. The titer of the AmC-1/ST-25 vaccine was $10^{8.0}TCID_{50}$/pig. The titer of the AmC-1/ST-50 vaccine was $10^{7.3}TCID_{50}$/pig. The pigs were inoculated with 1 ml orally and 1 ml intramuscularly. At two weeks post-vaccination, all animals were challenged with virulent Type-C rotavirus. Blood samples were collected at the time of vaccination, time of challenge (two weeks post-vaccination), and three weeks post-challenge.

Serum neutralizing antibody levels to Type-C rotavirus were determined by a varying serum constant virus assay. Briefly, serum dilutions were made and an equal volume of reference Type-C rotavirus was added to each dilution. The amount of virus used in the serum neutralization ranged from 300 to 1000 $TCID_{50}$'s per serum dilution. In addition, standard negative and positive serums were run in each assay. Virus-serum mixtures were incubated at 37@C. for 60 minutes and then inoculated onto confluent swine testicular cell cultures as described in Example 1. Cultures were examined for the presence of cytopathic effect at 5–7 days post-inoculation. Serum dilutions that exhibited cytopathic effect were scored as (+) and serum neutralization titers were calculated by the Spearman Karber method. The data are presented in Table 1.

TABLE 1

Anti-Type-C Porcine Rotavirus Serum Neutralizing Antibody Responses in Vaccinated CDCD Pigs

| No. of Pigs | Treatment | Type-C Rotavirus Serum Neutralizing Antibody Titers[1] | | |
|---|---|---|---|---|
| | | Prevac | Day of Challenge[2] | 3 Weeks Post-Challenge |
| 4 | C Rota/ST-25 | 35 | 550 | 640 |
| 4 | C Rota/ST-50 | 35 | 280 | 640 |
| 2 | Nonvaccinated | 40 | 35 | 280 |

[1]Group Geometric Mean Serum Neutralizing titers. Titers ≦ 40 are considered nonspecific.
[2]Day of Challenge: two weeks post-vaccination Both Type-C rotavirus vaccinated groups demonstrated seroconversions post-vaccination. Antibody levels for both vaccinated groups were at least eight times or more higher than the nonvaccinated control antibody levels.

Animals were observed for clinical signs of rotavirus infections twice daily. No animal exhibited clinical signs post-vaccination, thus further demonstrating the avirulence of the Type-C tissue culture passaged material. The data indicates that the virus has been so modified as to allow an immune response without virulence factors associated with disease. The immune response in vaccinated pigs was confirmed by substantial reduction in Type-C virus morbidity compared with nonvaccinated controls, as shown in Table 2.

TABLE 2

| Morbidity Incidence and Duration Post-Challenge | | |
|---|---|---|
| Group Nonvaccinated | MID[1] | % Reduction Compared to Controls |
| Nonvaccinated | 11/14(79%) | |
| Type-C/MA-25 | 0/28(0%) | 100% |
| Type-C/Ma-50 | 5/28(18%) | 77% |

[1]MID: Morbidity Incidence and Duration = Number of days pigs exhibited diarrhea/total number of pig days.

These data clearly demonstrate that the adaptation of Type-C rotavirus to swine testicular cells by the methods taught herein is not deleterious to its antigenicity, and that virus propagated in the diploid swine testicular cell line has led to an effective vaccine that can actively immunize pigs. Passage in swine testicular cells has thus been found to diminish or eliminate Type-C rotavirus virulence, without altering its immunogenicity.

An animal study was conducted to evaluate the safety and efficacy of the cell culture adapted C-rotavirus when incorporated into a multivalent rotavirus vaccine that contained two of the major porcine rotavirus Type-A fractions identified as OSU(A-1, serotype) and Iowa(A-2, serotype). The MLV Type-A rotavirus is a U.S.D.A. licensed vaccine for prevention of rotavirus infection, and is used in pregnant animals as well as in young pigs. The safety and efficacy of the Type-A rotavirus vaccine has been previously reported (15, 16, 34, 35).

The objective of the present study was to determine if animals vaccinated with the multivalent rotavirus vaccine would still seroconvert to Type-C rotavirus and whether or not they would be protected when challenged with Type-C rotavirus.

Ten CDCD pigs were used to evaluate the efficacy of the multivalent MLV rotavirus vaccine, four were nonvaccinated, and six were vaccinated. The amount of rotavirus used was as follows: $10^{7.1}TCID_{50}$ of A-1 pig, $10^{7.3}TCID_{50}$ of A-2/pig, $10^{8.3}$ $TCID_{50}$ of AmC-1(ST-passage-25) per pig. The pigs were given 1 ml orally and 1 ml intramuscularly. At fourteen days post-vaccination, all animals were orally challenged with virulent Type-C rotavirus.

Blood samples were collected at the time of vaccination and at the time of Type-C challenge (14 days post-vaccination). Serum neutralizing antibody levels to all rotavirus fractions were determined by the varying-serum constant-virus assay described above. The data are shown in Table 3.

TABLE 3

| | | CDCD Pig Serum Neutralizing Antibody Response to Multivalent MLV Rotavirus Vaccine | | | | | |
|---|---|---|---|---|---|---|---|
| No. of | | Type-C | | Type-A$_1$ | | Type-A$_2$ | |
| Pigs | Treatment | PreVac | 14-DPV[1] | PreVac | 14-DPV | PreVac | 14-DPV |
| 6 | MLV Rota | 40 | 363(9x)[2] | 35 | 2090(60x)[2] | 40 | 832(21x)[2] |
| 4 | NonVac's | 23 | 40(0x) | 35 | 40(0x) | 23 | 23(0x) |

[1]14-DPV: Fourteen days post-vaccination(Day of challenge with Type-C rotavirus).
[2](Nx): N-Fold increase in serum neutralizing titers.

It is apparent that Type-C rotavirus was still effective in the vaccinated animals when used in combination with the MLV Type-A rotavirus vaccine as measured by its ability to induce seroconversion.

All animals were observed for clinical sings of rotavirus infection twice daily post-vaccination. No animal exhibited clinical signs, thus demonstrating the safety of the Type-A and Type-C combination MLV vaccine. Further evidence of vaccine efficacy was observed after challenge of vaccinated or control pigs with virulent Type-C, A$_1$ and A$_2$ rotaviruses, as shown in Table 4.

ministered orally, by intramuscular, subcutaneous or intraperiteneal injection, or by intranasal innoculation.

Example 4

Vaccine Evaluation of Swine Testicular Cell Culture Adapted MLV Type-C Rotavirus: Passive Immunity Animal studies were conducted in pregnant gilts in order to evaluate the safety and efficacy of MLV Type-C rotavirus, either alone or as a component of a multivalent vaccine. A total of 28 pregnant gilts were used in these studies. Ten gilts were nonvaccinated; ten gilts were vaccinated with Type-C in a multivalent vaccine, and eight gilts were vaccinated with Type-C rotavirus alone. The multivalent vaccine contained MLV Type-C rotavirus, MLV Type-A rotaviruses, MLV TGE (Transmissible Gastroenteritis), *Clostridium perfringens* Type-C, and *Escherichia coli*. The Type-C vaccine was generated by methods described in Example 1, and was administered to pregnant gilts in one of two ways: (a) The vaccine was administered orally at five and three weeks followed by an intramuscular dose at one week prior to farrowing; or (b) The vaccine was administered intramuscularly at five and two weeks prior to farrowing.

The animals were bled prior to vaccination and on the day of farrowing. In addition, milk samples were collected on the day of farrowing (colostrum) and 7-14 days after farrowing. The serum and milk samples were

TABLE 4

| | Clinical Signs and Rotavirus Fecal Shedding Post-Challenge (Type-C, Type-A$_1$ and Type-A$_2$) | | | | | |
|---|---|---|---|---|---|---|
| | | | | Rotavirus Fecal Shedding[2] | | |
| | MID[1] Post-Challenge | | | Post-Challenge | | |
| Group | Type-C | Type-A$_1$ | Type-A$_2$ | Type-C | Type-A$_1$ | Type-A$_2$ |
| NonVaccinated Controls | 20/28(71%) | 24/28(86%) | 16/28(57%) | + | + | + |
| Combo Rota | 2/42(4%) | 0/42(0%) | 0/42(0%) | − | − | − |
| % Reduction Compared to NonVaccinated Controls | 94% | 100% | 100% | 100% | 100% | 100% |

[1]MID: Morbidity Incidence and Duration = Number of days pigs exhibited diarrhea/total number of pig days.
[2]Determined by IFA staining of infected cells and/or RNA extraction of fecal samples and PAGE analysis.

These data clearly illustrate nearly 100% protection from clinical signs of rotavirus disease and fecal virus shedding. These data also clearly indicate that Type-C, ST-cell culture adapted rotavirus can be used as a safe and effective vaccine for prevention of virulent Type-C rotavirus infections, even when added to a multivalent Type-A rotavirus vaccine.

The invention is not limited to any particular procedure for active immunization. The vaccine may be adassayed for anti Type-C serum neutralizing antibodies by methods described in Example 3. All vaccinated gilts farrowed normal and healthy litters, and no adverse vaccine reactions were observed. The addition of the Type-C MLV rotavirus to a multivalent vaccine did not reduce the effectiveness of the Type-C rotavirus, as shown in Table 5.

TABLE 5

Efficacy Evaluation of MLV Type-C Rotavirus Vaccines in Pregnant Swine.

| No. of Animals | Treatment | Group Geometric Mean Type-C Rotavirus Neutralizing Antibody Titers | | | |
|---|---|---|---|---|---|
| | | Serum PreVac | Serum Day of Farrow( )[1] | Colostrum( )[2] | 7-14 DPF Milk( )[3] |
| 10 | NonVaccinated | 126 | 189(0x) | 640 | 71 |
| 10 | C-rota/multivalent | 69 | 640(9x) | 3648(6x) | 363(5x) |
| 8 | C-rota/alone | 57 | 363(6x) | 3030(5x) | 245(3x) |

[1](Nx): N-Fold increase from Pre-Vac titer.
[2]( ): Fold increase in Colostral Geometric Mean Titer(GMT) compared to Nonvaccinated Control Group.
[3](Nx): N-Fold increase in Milk Geometric Mean Titer(GMT) compared to Nonvaccinated Control Group.

Vaccinated animals seroconverted to the Type-C rotavirus and had higher levels of colostral and milk neutralizing antibody titers than their nonvaccinated counterparts. This indicates that passive immunity to Type-C rotavirus for nursing pigs can be achieved by vaccination of pregnant gilts with either monovalent MLV Type-C rotavirus vaccine or a multivalent vaccine containing MLV Type-C rotavirus.

The present invention is not limited to the above protocol for passive immunization. For example, both oral and intramuscular doses may be administered 2-3 weeks before farrowing.

Example 5

Vaccine Evaluation of Tissue Culture Adapted Type-C Rotavirus Killed Vaccine: Passive Immunity

Animal studies were conducted in pregnant gilts in order to evaluate the safety and efficacy of a killed Type-C rotavirus vaccine either alone or as a component of a multivalent vaccine. A total of ten pregnant gilts were used in the studies. Four gilts were not vaccinated, three gilts were vaccinated with Type-C rotavirus contained in a multivalent vaccine, and three gilts were vaccinated with Type-C rotavirus vaccine alone. All vaccinated animals farrowed normal healthy litters, and no adverse reactions were observed due to vaccination. The Type-C vaccine was generated by methods described in Example 1. The cell debris was removed by centrifugation and the supernatant was collected. The Type-C rotavirus bulk was then inactivated with 0.1% formalin for five days at 37° C. Type-C rotavirus bulk was identified in the killed virus bulk by RNA extraction PAGE analysis.

The killed vaccine was administered intramuscularly at five and two weeks prior to farrowing. The animals were bled prior to vaccination and on the day of farrowing. In addition, milk samples were collected on the day of farrowing (colostrum) and 7-14 days after farrowing. The serum and milk samples were assayed for rotavirus Type-C neutralizing antibodies by methods described in Example 3.

The addition of the killed Type-C rotavirus to a multivalent vaccine did not reduce the effectiveness of the Type-C rotavirus. Vaccinated animals seroconverted to the Type-C rotavirus and had higher levels of colostral and milk serum neutralizing antibody titers than their nonvaccinated counterparts.

The data are presented in Table 6.

TABLE 6

Efficacy Evaluation of Killed type-C Rotavirus Vaccines in Pregnant Swine

| No. of Animals | Treatment | Group Geometric Mean Type-C Rotavirus Neutralizing Antibody Titers | | | |
|---|---|---|---|---|---|
| | | Serum PreVac | Serum Day of Farrow( )[1] | Colostrum( )[2] | 7-14 DPF Milk( )[3] |
| 4 | NovVaccinated | 53 | 91(0x) | 832 | 69 |
| 3 | C-rota/multivalent | 130 | 640(5x) | 2750(3x) | 279(4x) |
| 3 | C-rota/alone | 91 | 550(6x) | 3630(4x) | 363(5x) |

[1](Nx): N-Fold increase from Pre-Vac titer.
[2]( ): Fold increase in Colostral Geometric Mean Titer (GMT) compared to Nonvaccinated Control Group.
[3](Nx): N-Fold increase in Milk Geometric Mean Titer (GMT) compared to Nonvaccinated Control Group.

It is apparent from the data presented in Table 6 that the killed Type-C rotavirus vaccine (either alone or in combination with a multivalent vaccine) can be effectively used to boost the immunity of a pregnant animal to Type-C rotavirus and consequently increase the level of passive immunity provided to the nursing pigs.

These data clearly demonstrate that the adaptation of Type-C rotavirus to a diploid swine testicular cell line by the method of the present invention is not deleterious to its antigenicity, and that virus propagated in swine testicular cells by the technique of the present invention may lead to effective vaccines, either MLV or killed vaccines, against virulent Type-C rotavirus infections. Passage in swine testicular cell culture has been found to diminish or eliminate Type-C rotavirus virulence, without altering its immunogenicity.

Example 6

Testing of Cell Lines for Type-C Rotavirus Infectivity

Studies were conducted with virulent Type-C rotavirus intestinal contents generated in gnotobiotic pigs. Intestinal contents were inoculated onto confluent monolayers of the cell lines mentioned below. Inoculated cells were incubated for 2-days then fixed in acetone and examined for virus infectivity by indirect immunofluorescence.

| Cell Line | Type | Percent of monolayer infected(IFA)[1] | CPE 5th/Pass |
|---|---|---|---|
| Swine Testicular | Diploid | 75% | Positive |
| MA-104 | Stable | 15% | Have not done |
| Vero | Stable | 8% | Have not done |
| Bovine Turbinate | Stable | 8% | Have not done |
| PK$_{15}$ | Stable | 0% | Have not done |
| BSC | Stable | 0% | Have not done |

[1]IFA: Indirect immunofluorescent staining of inoculated cells 48-hours post-inoculation.

Modification

Vaccines are prepared using an effective amount of the Type-C rotavirus prepared according to the present invention in a pharmaceutically acceptable carrier. Depending upon the type of administration proposed for the vaccine, the carrier may be one suitable for oral, intramuscular, or other conventional type of vaccine administration. For a modified live virus vaccine, the virus is preferably lyophilized and stabilized with sucrose, gelatine and peptone. For a killed virus vaccine, preferred carriers are Freund's complete or incomplete adjuvants, squalane, and aqueous aluminum hydroide. Moreover, the Type-C rotavirus produced by the present invention may be incorporated in any conventional multivalent vaccine formulations including with Type-A rotavirus, transmissible gastroenteritis, *Clostridium perfringens* Type-C, and *Escherichia coli*, either alone or in any suitable combination thereof.

The Type-C rotavirus antigen produced according to the present invention can be used in diagnostic tests to diagnose infections with Type-C rotavirus. These types of immunological tests are well known to those skilled in the art, and include RIA, ELISA, immunofluorescence, chemiluminescence, and the like. Crude or purified Type C rotavirus antigens may also be used as immunogenic agents in the production of antibody-containing fluids or in the vaccination of susceptible subjects against Type C rotavirus, or as immunosorbents in the purification of Type C rotavirus-specifc antibodies. These antibodies, in turn, may be used therapeutically as a substitute for or in addition to induction of an immune response by vaccination. The antibodies may be administered in the form of immune serum or milk, or in a more purified form.

While Type-C rotavirus particles may be obtained from the culture media used to support the growth of the host cells, yields are improved if the host cells are lysed, e.g., by several freeze-thaw cycles or by sonication. The viral fluids are then purified from the cellular debris, e.g., by centrifugation at 2,000 to 6,000 xg. Optionally, the virus may be further purified, e.g., by ultracentrifugation at 100,000 xg through a 20% sucrose cushion and resuspended in physiological saline. The resulting antigenic preparation may then be labeled or immobilized for diagnostic use.

Alternatively, the preparation may be further treated with, e.g., chelating agents and/or detergents, to produce subunit antigens, or chromatographically resolved by, e.g., gel filtration, ion exchange chromatography, lectin affinity chromatography, reverse phase HPLC, etc. into component antigenic molecules.

The diagnostic assays of the present invention are not limited to any particular assay format. Instead of a fluoroimmunoassay as in Example 2, an enzyme immunoassay, radioimmunoassay, particle (e.g., latex) agglutination assay, etc. might be employed. The assay may be in a competitive or a sandwich format and a labeled antigen may be employed instead of a labeled anti-antibody. For an EIA, the preferred labels are alkaline phosphatase and horseradish perodixase. For an RIA, the preferred label is $I^{125}$. Avidin-biotin linkages may be used to conjugate a labeled species (or a support) to an immunoreagent.

Diagnostic kits are prepared from antigens prepared according to the present invention by packaging the antigens in suitable containers in suitable diluents, along with the desired reagents and optional supports.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

REFERENCES

1. Bellinzoni, N., Mattion, L., Vallejos, J., LaTorre, E., Scodeller, A. 1987. Atypical Rotavirus in Chickens in Argentina. Res. Vet Science, 43:130–131.
2. Benfield, D. A., Stotz, Ivan., Moore, R. and McAdaragh, John P. 1982. Shedding of Rotavirus in Feces of Sows Before and After Farrowing. J. Clin. Microbiol., 16:186–190.
3. Bohl, E. H., Kohler, E. M., Saif, L. J., Cross, R. F., Agnes, A. G. and Theil, K. W. 1978. Rotavirus as a Cause of Diarrhea in Pigs. J. Am. Vet. Med. Assoc., 172:458–463.
4. Bohl, E. H., Saif, L. J., Theil, K. W., Agnes, A. G., and Cross R. F., 1982. Porcine Pararotavirus: Detection, Differentiation from Rotavirus, and Pathogenesis in Gnotobiotic Pigs. J. Clin. Micro., 15:312–319.
5. Breer, C., Wunderli, W., Lee, C., Weisser, E., and Schopfer, K., 1985. Rotavirus-und Pararotavirus-Infectionen bei Erwachsenen. Schweiz. med. Wschr. 115:1530–1535.
6. Bremont, M., Cohen, J., McCrae, M. A., 1988. Analysis of the Structural Polypeptides of a Porcine Group C Rotavirus. J. Virol., 62:2183–2185.
7. Bridger, J. C., Pedley, S., McCrae, M., 1986. Group C Rotaviruses in Humans. J. Clin. Micro. 23:760–763.
8. Bridger, J. C. 1988. Porcine Rotaviruses and their Role in Disease. Pig News and Information, 9:23–26.
9. Bridger, J. C., 1985. Prevalence of Antibody to Typical and Atypical Rotaviruses in Pigs. Vet. Rec. 116:50.
10. Bridger, J. C., 1987. Novel Rotaviruses in Animals and Man. 1987 Novel Diarrhoea Viruses. Wiley, Chichester Ciba Foundation Symposium 128:5–23.
11. Brown, D. W., Beards, G. M., Guang-Mu, C., Flewett, T. H., 1987. Prevalence of Antibody to Group B (Atypical) Rotavirus in Humans and Animals;. J. Clin. Micro., 25:316–319.
12. Brown, D. W. G., Mathan, M. M., Martin, R.; Beards, G. M., Mathan, V. I., 1988. Rotavirus epidemiology in Vellore, South India: Group, Subgroup, Serotype, and Electropherotype. J. Clin. Micro 26:2410–2414.

13. Dimitrov, D. H., Estes, M. K., Rangelova, S. M., Shindarov, L. M., Melnick, J. L., and Graham, D. Y. 1983. Detection of Antigenically Distinct Rotavirus from Infants, Infect. and Immun. 44:2. 523-526.
14. Espejo, R. T., Puerto, F., Soler, C., and Gonzalez, N., (1984), Characterization of a Human Pararotavirus, Infect. and Immun. 44 (1):112-116.
15. Fitzgerald, G. R., Welter, M. W. and Welter, C. J. 1986. Evaluating the Performance of a Porcine Rotavirus Vaccine. Vet. Med., 81:188-192.
16. Fitzgerald, G. R., Welter, M. W. and Welter, C. J. 1986. Effect of Porcine Rotavirus Vaccination on Postweaning Weight Gains in Baby Pigs. Modern Vet. Pract., 67:609-610.
17. Fitzgerald, G. R., Barker, T., Welter, M. W. and Welter, C. J. 1988. Diarrhea in Young Pigs: Comparing the Incidence of the Five Most Common Infectious Agents. Vet. Med., 83:80-86.
18. Jashes, M. Sandino, A. M., Faundez, G, Avendano, L. F., Spencer, E., 1986. In Vitro Transcription of Human Pararotavirus. J. Virol. 57:183-190.
19. Kapikian, A. Z., Fores, J., Hoshino, Y., Midthun, K., Gorziglia, M., Green, K. Y., Chanock, R. M., Potash, L., Sears, S. D., Clements, M. L., Halsey, N. A., Black, R. E., Perez-Schael, I., 1989. Prospects for Development of a Rotavirus Vaccine Against Rotavirus Diarrhea in Infants and Young Children. Rev. of Infect. Dis. Vol. II, Supplement 3:S539-546.
20. Matsumoto, K., Motoichi, H., Shudo, V., Shuji, N., Shunzo, C., and Yoshinobu, K. 1989. An Outbreak of Gastroenteritis Associated with Acute Rotaviral Infection in School children. J. of Infect. Dis. 160 (4):611-615.
21. Nagesha, H. S., Hum, C. P., Bridger, J. C., Holmes, I. H., 1988. Atypical Rotaviruses in Australian Pigs. Arch. Virol. 102:91-98.
22. Nicolas, J. C., Cohen, J., Fortier, B., Lourenco, M. H., and Bricout, F. 1982. Isolation of a Human Pararotavirus. Virology 124:181-184.
23. Ojeh, C. K., Saif, L. J. Kang, S. Y., 1988. Production and Characterization of Monoclonal Antibodies to Porcine Group C Rotavirus. Conference of Research Workers in Animal Disease, Nov. 14-15, Abstract #328.
24. Pedley, S., Bridger, J. C., Brown, J. F., McCrae, M. A., 1983. Molecular Characterization of Rotaviruses with Distinct Group Antigens. J. Gen. Virol., 64:2093-2101.
25. Penaranda, M. E., Cubitt, W. D., Sinarachatanant, P., Taylor, D. N., Likanonsakul, S., Saif, L., Glass, R. I., 1989. Group C Rotavirus Infections in Patients with Diarrhea in Thailand, Nepal and England. J. Infect. Dis. 160:392-397.
26. Rodger, S. M., Bishop, R. F., Holmes, I. H., 1982. Detection of a Rotavirus-Like Agent Associated with Diarrhea in an Infant J. Clin. Micro. 16:724-726.
27. Saif., L. J., and Theil, K. W., 1985. Antigenically Distinct Rotaviruses of Human and Animal Origin. Elsevier 208-214.
28. Saif, L. J., Terret, L. A., Miller, K. L., and Cross, R. F. 1988. Serial Propagation of Porcine Group C Rotavirus (Pararotavirus) in a Continuous Cell Line and Characterization of the Passaged Virus. J. of Clin. Micro. 26 (7):1277-1282.
29. Snodgrass, D. R., Herring, A. J., Campbell, I., Inglis, J. M., Hargreares, F. D. 1984. Atypical Rotaviruses from Calves, Piglets, Lambs and Man. J. Gen. Vir., 65:909-914.
30. Terret, L. A., and Saif, L. J., (1987), Serial Propagation of Porcine Group C Rotavirus (Pararotavirus) in Primary Porcine Kidney Cell Culture, J. Clin. Micro., 25:1316-1319.
31. Terret, L. A., Saif, L. J., Theil, K. W., and Kohler, E. M. 1987. Physicochemical Characterization of Porcine Pararotavirus and Detection of Virus and Viral Antibodies Using Cell Culture Immunofluorescence, J. Clin. Micro. 25 (2):268-272.
32. Theil, K. W., McCloskey, C. M., Saif, L. J., Redman, D. R., Bohl, E. H., Hancock, D. D., Kohler, E. M., Moorhead, P. D. 1981. Rapid, Simple Method of Preparing Rotaviral Double-Stranded Ribonucleic Acid for Analysis by Polyacrylamide Gel Electrophoresis. J. Clin. Micro. 14:273-280.
33. Ushijima, H., Honma, H., Mukoyama, A., Shinozaki, T., Fujita, Y., Kobayashi, M., Ohseto, M., Morikawa, S., and Kitamura, T., (1989), Detection of Group C Rotaviruses in Tokyo, J. of Med. Vir. 27:299-303.
34. Von Bonsdorff, C., Svensson, L., Human Serogroup C Rotavirus in Finland, (1988), Scand. J. of Infect. Dis. 20:475-478.
35. Welter, M. W., Fitzgerald, G. R., and Welter, C. J. 1986. A Combination Porcine Rotavirus Vaccine Against Two Major Type-A Serotypes. Agri. Practice Swine Immunology. 7:59-62.
36. Welter, M. W., Welter, C. J., Evaluation of Killed and Modified Live Porcine Rotavirus Vaccines in Cesarean Derived Colostrum Deprived Pigs. Vet Micro. "In Press"
37. Woode, G. N., Bridger, J. C., Hall, G. A., Jones J. M. and Jackson, G. 1976. The Isolation of Reovirus-Like Agents (Rotaviruses) from Acute Gastroenteritis of Piglets. J. Med. Microbiol., 9:203-209.
38. U.S. Pat. No. 3,838,004, Mebus and Twiehaus, Sep. 24, 1974, Calf Diarrhea Virus Vaccine and Processes.
39. U.S. Pat. No. 3,839,556, Mebus and Twiehaus, Oct. 4, 1974, Calf Diarrhea Virus Vaccine and Processes.
40. U.S. Pat. No. 3,869,547, Mebus et al, Mar. 4, 1975, Calf Diarrhea Virus Vaccine and Processes.
41. U.S. Pat. No. 4,751,080, Wyatt et al, Jun. 14, 1988, Vaccine Against Rotavirus Diseases.
42. U.S. Pat. No. 4,624,850, Albert et al., Nov. 25, 1986, Live Attenuated Human Rotavirus Vaccine.

What is claimed is:

1. A method for propagating a Group C rotavirus in cell culture which comprises passaging a Group C rotavirus in swine testicular cells capable of supporting the growth of the virus for at least five passages, said cells being provided with a medium which supports the growth of the cells and is further characterized as having a non-cytopathic amount of proteolytic enzymes which can exert a cytopathic effect on said rotavirus.

2. The method according to claim 1 wherein the growth medium includes trypsin.

3. The method according to claim 2 wherein the trypsin is present in amounts ranging from about 10 to less than 80 µg/ml.

4. The method of claim 1 wherein said rotavirus is serially passaged in ST cells until it has become essentially non-pathogenic without substantial loss of immunogenicity.

5. The method of claim 1 wherein said rotavirus is serially passaged for at least about 22 passages in ST cells.

6. The method of claim 5 wherein said rotavirus is serially passaged for at least about 30 passages in ST cells.

7. The method of claim 1 wherein the culture medium includes a proteolytic enzyme.

8. The method of claim 1 wherein the medium is essentially free of pancreatin and pancreatin components other than trypsin.

9. The method according to claim 1 wherein the pH ranges from about 6 to about 8.

10. The method of claim 1 wherein the cytopathic effect of the Group C rotavirus is observed periodically to confirm successful passage of the virus., 11. A method for propagating a Group C rotavirus in cell culture which comprises passaging a Group C rotavirus in swine testicular cells capable of supporting the growth of the cells for at least five passages, said cells being provided with a medium which supports the growth of the cells in which proteolytic enzymes are present in a total amount which is less than about 80 $\mu$g/ml.

12. A vaccine comprising an immunologically effective amount of a Group C rotavirus propagated according to claim 1 in a pharmaceutically acceptable carrier, said virus having been rendered essentially nonpathogenic.

13. An attenuated vaccine comprising an effective amount of a Group C rotavirus propagated according to claim 4, said propagation having rendered the virus essentially nonpathogenic, in a pharmaceutically acceptable carrier.

14. An attenuated vaccine comprising an effective amount of a Group C rotavirus propagated according to claim 5, said propagation having rendered the virus essentially nonpathogenic, in a pharmaceutically acceptable carrier.

15. A killed vaccine comprising an effective amount of a Group C rotavirus propagated according to claim 1 and subsequently inactivated to render the virus essentially nonpathogenic, in a pharmaceutically acceptable carrier.

16. A method for immunizing a human or animal for an infection caused by a Group C rotavirus comprising administering to said human or animal a vaccine according to claim 12.

17. A method of protecting neonatal nursing mammals from an infection caused by a Group C rotavirus comprising administering to pregnant host mammals within six weeks prior to parturition a vaccine according to claim 12, thereby inducing an immune response in said host, whereby passive protection from said infection is provided by the colostrum and milk fed by said host to neonatal nursing mammals.

18. An immunogenic composition comprising one or more Type C rotavirus antigens obtained by a process comprising propagating a Type C rotavirus according to the method of claim 1 and lysing the host cells, and a pharmaceutically acceptable carrier, said composition being capable of raising antibodies in an immunocompetent subject, said antibodies being immunologically reactive with Type C rotavirus.

19. A method for immunizing a human or animal which comprises administering an immunogenic composition according to claim 18.

* * * * *